(12) United States Patent
Guo et al.

(10) Patent No.: US 10,551,197 B2
(45) Date of Patent: Feb. 4, 2020

(54) MOBILE X-RAY EXAMINATION APPARATUS

(71) Applicant: SIEMENS HEALTHCARE GmbH, Erlangen (DE)

(72) Inventors: Qiang Guo, Shanghai (CN); Yi Hua Jiang, Shanghai (CN); Ao Lin Tang, Shanghai (CN)

(73) Assignee: Siemens Healthcare GmbH, Erlangen (DE)

( * ) Notice: Subject to any disclaimer, the term of this patent is extended or adjusted under 35 U.S.C. 154(b) by 177 days.

(21) Appl. No.: 15/550,258

(22) PCT Filed: Feb. 11, 2016

(86) PCT No.: PCT/EP2016/052942
§ 371 (c)(1),
(2) Date: Aug. 10, 2017

(87) PCT Pub. No.: WO2016/128525
PCT Pub. Date: Aug. 18, 2016

(65) Prior Publication Data
US 2018/0031377 A1    Feb. 1, 2018

(30) Foreign Application Priority Data
Feb. 12, 2015   (CN) .......................... 2015 1 0075128

(51) Int. Cl.
*G01C 21/30*   (2006.01)
*A61B 6/00*    (2006.01)
*G05D 1/02*    (2006.01)

(52) U.S. Cl.
CPC .......... *G01C 21/30* (2013.01); *A61B 6/4405* (2013.01); *A61B 6/4441* (2013.01); *G05D 1/024* (2013.01);
(Continued)

(58) Field of Classification Search
CPC .... G01C 21/30; G01C 21/206; A61B 6/4405; A61B 6/4441; G01T 7/00
See application file for complete search history.

(56) References Cited

U.S. PATENT DOCUMENTS 5,936,240 A * 8/1999 Dudar ...................... G01V 5/02
250/253
6,834,220 B1 * 12/2004 Bail .......................... G01S 1/08
180/167
(Continued)

FOREIGN PATENT DOCUMENTS

| EP | 2058720 A2 | 5/2009 |
| EP | 2380496 A1 | 10/2011 |
| EP | 2815951 A2 | 12/2014 |

*Primary Examiner* — David P Porta
*Assistant Examiner* — Jeremy S Valentiner
(74) *Attorney, Agent, or Firm* — Schiff Hardin LLP

(57) ABSTRACT

A mobile X-ray examination apparatus has an instruction receiving device that receives an entered instruction for the mobile X-ray examination apparatus to reach a designated position. A navigation device creates an environment map of an environment of the mobile X-ray examination apparatus, determines a current position of the mobile X-ray examination apparatus according to detected environment profile information, calculates a movement trajectory of the mobile X-ray examination apparatus according to the environment map, the current position and the designated position received by the instruction receiving device, and sends corresponding information to a central control device. The central control device causes the mobile X-ray examination apparatus to reach the designated position along the movement trajectory according to the corresponding information sent by the navigation device.

13 Claims, 4 Drawing Sheets

(52) U.S. Cl.
CPC ... *G05D 1/0274* (2013.01); *G05D 2201/0206* (2013.01)

(56) References Cited

U.S. PATENT DOCUMENTS

| | | | |
|---|---|---|---|
| 2001/0044577 A1 | 11/2001 | Braun et al. | |
| 2008/0114545 A1* | 5/2008 | Takaoka | G01C 21/265 701/526 |
| 2010/0296632 A1* | 11/2010 | Bouvier | A61B 6/4405 378/198 |

* cited by examiner

MOBILE X-RAY EXAMINATION APPARATUS

BACKGROUND OF THE INVENTION

Field of the Invention

The present invention relates to X-ray examination apparatuses, in particular a mobile X-ray examination apparatus.

Description of the Prior Art

A mobile X-ray examination apparatus is an apparatus that is commonly used in the course of medical treatment. A mobile X-ray examination apparatus generally has a very large volume and is heavy, so requires a relatively large effort to be moved. At present, most mobile X-ray examination apparatuses can only be moved from one site to another by hand, for example by pushing or pulling. This is physically demanding for a user. Some mobile X-ray examination apparatuses may be equipped with a pulling electric motor, which is driven by a user pressing a button or using a control stick.

SUMMARY OF THE INVENTION

An object of the present invention is to provide a mobile X-ray examination apparatus that makes movement less intensive for a user.

A mobile X-ray examination apparatus in accordance with the invention has an apparatus body with an X-ray source and an X-ray detector mounted thereon. An instruction receiving device is also situated on the apparatus body, that receives an instruction, entered therein as an input, that instructs the apparatus body to reach a designated position. Also situated on the apparatus body is a navigation device, to which the instruction receiving device sends the aforementioned instruction. The navigation device is designed to create an environment map of an environment of the mobile X-ray examination apparatus, and to determine a current position of the mobile X-ray examination apparatus (i.e. the apparatus body thereof) according to detected environment profile examination. The navigation device is also designed to calculate a movement trajectory (path) of the mobile X-ray examination apparatus (i.e. the apparatus body thereof) according to the environment map, the current position, and the designated position received from the instruction receiving device. The navigation device is designed to send an electronic designation of the calculated movement trajectory to a central control device, also situated on the apparatus body. The central control device operates a drive device that in turn drives a transport device of the apparatus body in order to follow the calculated movement trajectory so as to reach the designated position.

The environment map of the environment of the mobile X-ray examination apparatus, the current position thereof and the movement trajectory are displayed on a touch screen of the mobile X-ray examination apparatus.

The navigation device includes a navigation controller and a detection device, wherein the detection device is an optical detection and distance-measuring sensor, mounted in front of the mobile X-ray examination apparatus in the direction of travel, and emits a series of coded laser pulses at intervals of a certain angle in a plane in space to detect in real time the environment of the mobile X-ray examination apparatus.

The navigation device is removably mounted on a body of the mobile X-ray examination apparatus.

The navigation controller calculates relative positions of an obstacle and the mobile X-ray examination apparatus according to an angle of a laser pulse emitted by the optical detection and distance-measuring sensor and a time difference between emission of the laser pulse and back-reflection thereof by the obstacle after encountering the obstacle, and finds a route by which the obstacle can be avoided.

The navigation controller obtains profile information about surrounding obstacles according to a laser pulse emitted by the optical detection and distance-measuring sensor and a laser pulse that is reflected back, and according to the profile information, performs matching with the environment map, to locate the mobile X-ray examination apparatus.

The mobile X-ray examination apparatus further has a notification device, for issuing prompt information when the mobile X-ray examination apparatus cannot find a route by which an obstacle can be avoided.

As noted, mobile X-ray examination apparatus has a movement device, and the navigation controller obtains real-time movement information of the movement device, and uses a Kalman filter to obtain the current position of the mobile X-ray examination apparatus.

The map created of the environment of the mobile X-ray examination apparatus is created by offline importing and/or by causing the mobile X-ray examination apparatus to traverse all reachable positions in the environment of use thereof in advance.

As noted, the mobile X-ray examination apparatus has a drive device, which may be a DC motor, such as a DC brushed motor or brushless motor, or a hub motor is used directly.

The mobile X-ray examination apparatus according to the present invention reduces the intensity of labor needed for the mobile X-ray examination apparatus for a user.

DESCRIPTION OF THE PREFERRED EMBODIMENTS

The present invention is described in further detail below by way of embodiments, to explain the object, technical solution and advantages thereof.

Figure 1:
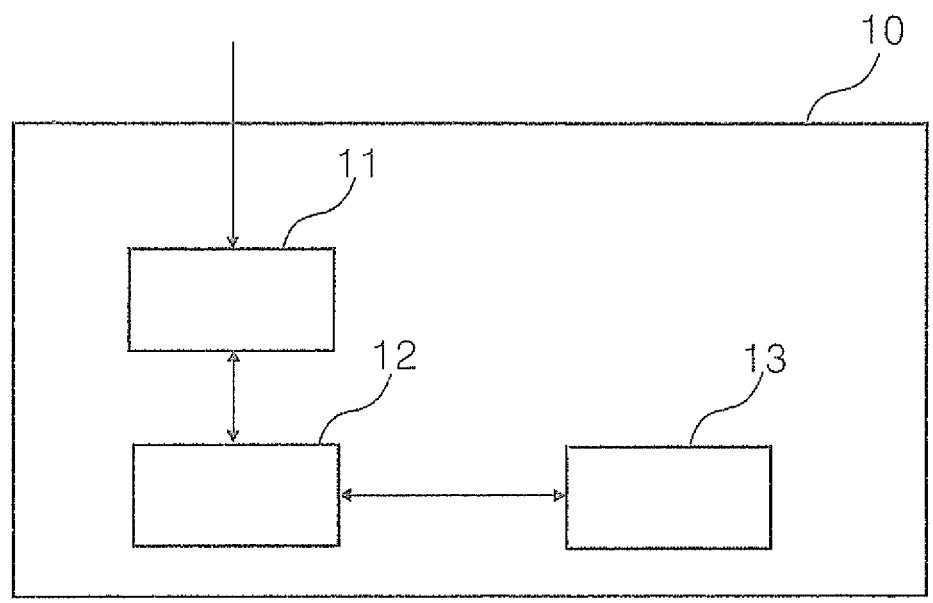
FIG. 1 is a block diagram of a mobile X-ray examination apparatus according to an embodiment of the present invention.
Figure 2:
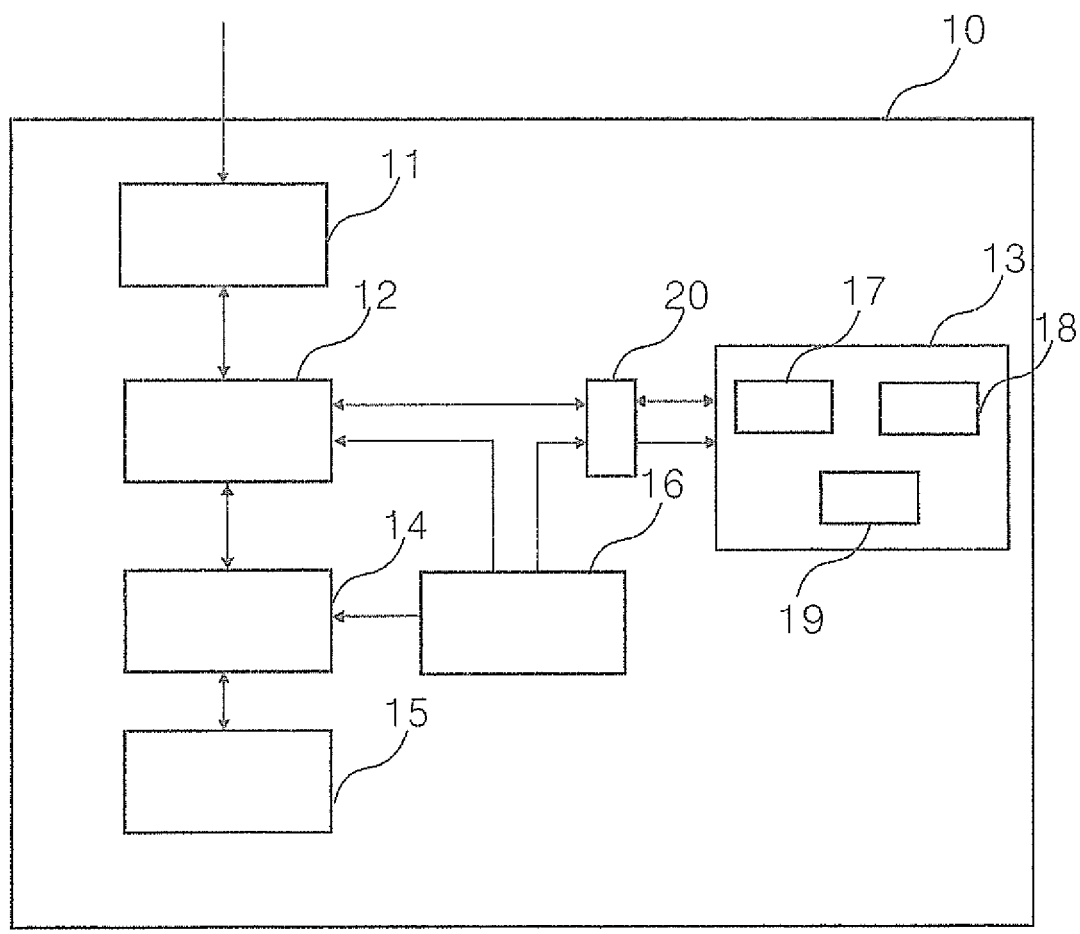
FIG. 2 is a block diagram of a mobile X-ray examination apparatus according to an embodiment of the present invention.

FIG. 1 is a block diagram of a mobile X-ray examination apparatus having an automatic navigation function according to an embodiment of the present invention. FIG. 2 is a block diagram based on FIG. 1 of a mobile X-ray examination apparatus according to an embodiment of the present invention. The mobile X-ray examination apparatus of the present invention is explained below in conjunction with FIGS. 1 and 2.

As FIG. 1 shows, the mobile X-ray examination apparatus 10 has an apparatus body 30 (see FIG. 3) with an X-ray source and an X-ray radiation detector mounted thereon, and an instruction receiving device 11, a central control device 12 (computer), and a navigation device 13 also mounted on or situated on the apparatus body 30.

Once the mobile X-ray examination apparatus 10 has been powered on, if the mobile X-ray examination apparatus 10 needs to be moved to a designated position, a user can make an input entry, via the instruction receiving device 11, of an instruction to reach the designated position. The instruction receiving device 11 is for example a touch screen on the mobile X-ray examination apparatus 10. A map of all positions reachable by the mobile X-ray examination apparatus (e.g. various examination rooms in a hospital) may be displayed on the touch screen; a doctor may open a corresponding setting interface by clicking a mouse or touching, to designate the designated position which the mobile X-ray examination apparatus 10 must reach. The designated position is transferred to the central control device 12, and transmitted into the navigation device 13 to be processed. The central control device 12 is a central control device for all function sub-systems of the mobile X-ray examination apparatus 10.

The navigation device 13 has a navigation controller 17, a detection device 18 and a storage device 19 (see FIG. 2), and can create or update an environment map of the environment of the mobile X-ray examination apparatus 10. The environment map may be imported offline and/or created online. The manner of offline importing may be, for example, to obtain in advance a map of the environment in which the mobile X-ray examination apparatus 10 is used, processing the map, and then storing it in the storage device 19 of the navigation device 13. The storage device 19 can be any of various types of memory, including a floppy disk, a hard disk, a magneto-optical disk, an optical disk (e.g. CD-ROM, CD-R, CD-RW, DVD-ROM, DVD-RAM, DVD-RW, DVD+RW), a magnetic tape, a non-volatile memory card, and a ROM. The manner of online creation is, for example, for a technician to manually push the mobile X-ray examination apparatus 10 so as to traverse once all reachable positions in the environment of use thereof (e.g. a hospital), and automatically generating an environment map by means of the data acquired.

Once the navigation controller 17 in the navigation device 13 has obtained the designated position entered by the user at the instruction receiving device 11, the current position of the mobile X-ray examination apparatus 10 is calculated based on real-time detection data (described in detail below) of the detection device 18. Once the current position of the mobile X-ray examination apparatus 10 has been obtained, the navigation controller 17 will further calculate a smooth route by which the designated position can be reached, according to the environment map and the designated position of the mobile X-ray examination apparatus 10. Based on this route, the navigation controller 17 can further determine current apparatus movement control information, and return this information to the central control device 12, which controls the drive device 14 (see FIG. 2) to drive the movement device 15 (see FIG. 2) so as to travel along the calculated route.

The detection device 18 in the navigation device 13 is used for locating the mobile X-ray examination apparatus 10 and measuring the environment thereof, and may be various types of sensor, and be one or more in number, e.g. an optical detection and distance-measuring sensor in the class of laser sensors. The laser sensor is mounted, for example, so as to face the region in front of the mobile X-ray examination apparatus 10 in the direction of travel. When the mobile X-ray examination apparatus 10 is stationary or traveling, the laser sensor may emit a series of coded laser pulses periodically at intervals of a certain angle, in a spatial plane e.g. in a horizontal plane. When a laser pulse shines onto an obstacle in front of the laser sensor, the laser pulse will be reflected back by the obstacle. Based on the angle at which the laser pulse was emitted and the time difference between emission and back-reflection of the laser pulse, the relative positions of the obstacle and the sensor or mobile X-ray examination apparatus can be calculated. This information about relative positions will be processed by the navigation controller 17 in the navigation device 13. The navigation controller 17 combines all information obtained about obstacles, and can thereby obtain profile information about surrounding obstacles, e.g. shape, direction, position etc. of obstacles. Furthermore, the obstacle profile information obtained is matched with the environment map, and the navigation controller 17 can thereby locate the mobile X-ray examination apparatus 10. If the navigation controller 17 can further obtain real-time movement information (e.g. learn the speed and acceleration thereof from an encoder) of the movement device 15 (e.g. wheels mounted at the bottom of the mobile X-ray examination apparatus), then the current position of the mobile X-ray examination apparatus 10 can be obtained more precisely by means of a Kalman filter.

In a hospital, there are many dynamic factors, such as patients, trolleys, etc., and these dynamic factors are always moving. The mobile X-ray examination apparatus 10 of the present invention can likewise process such a situation. When traveling on the predetermined route, the mobile X-ray examination apparatus 10 detects these dynamic obstacles in real time, and when an obstacle is discovered, the navigation device 13 will amend the route, to avoid the obstacle. If it is impossible to find a movement route by which the obstacle can be avoided, the navigation device 13 may send relevant information to the central control device 12. The central control device 12 may control the mobile X-ray examination apparatus 10 to temporarily stop traveling according to the relevant information, and issue prompt information and/or an acoustic/optical alert by means of a loudspeaker and/or a display screen, to notify the user, who then finds a new traveling route manually.

The navigation device 13 is connected to the central control device 12 and an energy supply device 16 (see FIG. 2) by means of an interface 20, thereby facilitating mounting and removal of the navigation device 13. The interface 20 chiefly fulfills two major functions: communication and power supply. Various buses or ethernet etc. may be used for communication between the navigation device 13 and the central control device 12, with the corresponding interfaces being bus and network interfaces etc. The energy supply device 16 provides a DC voltage-stabilized power supply for the navigation device 13 directly by means of a corresponding power supply interface on the interface 20.

Figure 3:
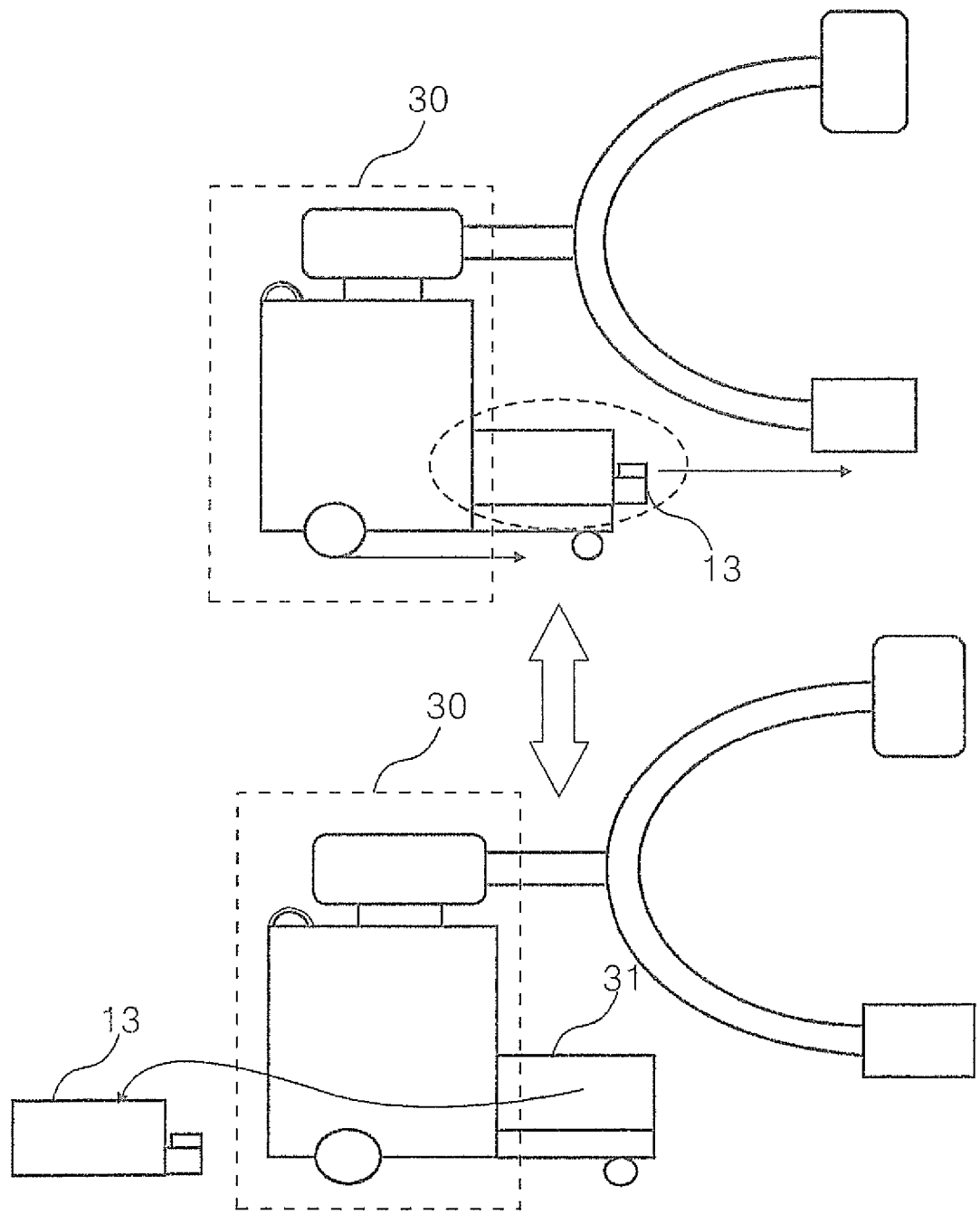
FIG. 3 is a schematic illustration of a mobile X-ray examination apparatus having a removable navigation device according to an embodiment of the present invention.

As FIG. 3 shows, the navigation device 13 may be a device which can be independently plugged in and taken out or removed, and can be conveniently mounted on a body 30 of the apparatus 10 or removed therefrom. In FIG. 3, the navigation device 13 is for example mounted in an accommodating space 31 on the body 30 of the X-ray examination apparatus 10.

Thus, one navigation device 13 may be suitable for different mobile X-ray examination apparatuses. For example, navigation of different mobile X-ray examination apparatuses can be accomplished by setting uniform electrical and mechanical interfaces for different mobile X-ray examination apparatuses, and by changing parameter settings (e.g. model number and motor parameters of the mobile X-ray examination apparatus) of the navigation device.

The drive device 14 is for example a DC motor, e.g. a DC brushless motor, brushed motor or hub motor. The movement device 15 is for example four wheels mounted on a chassis of the mobile X-ray examination apparatus 10, including two driving wheels and two driven wheels. The driving wheels drive the driven wheels to rotate under the drive of the drive device 14.

Each device in the mobile X-ray examination apparatus 10 is provided with the power supply needed during movement by the energy supply device 16, which may be a storage battery or a supercapacitor.

Figure 4:
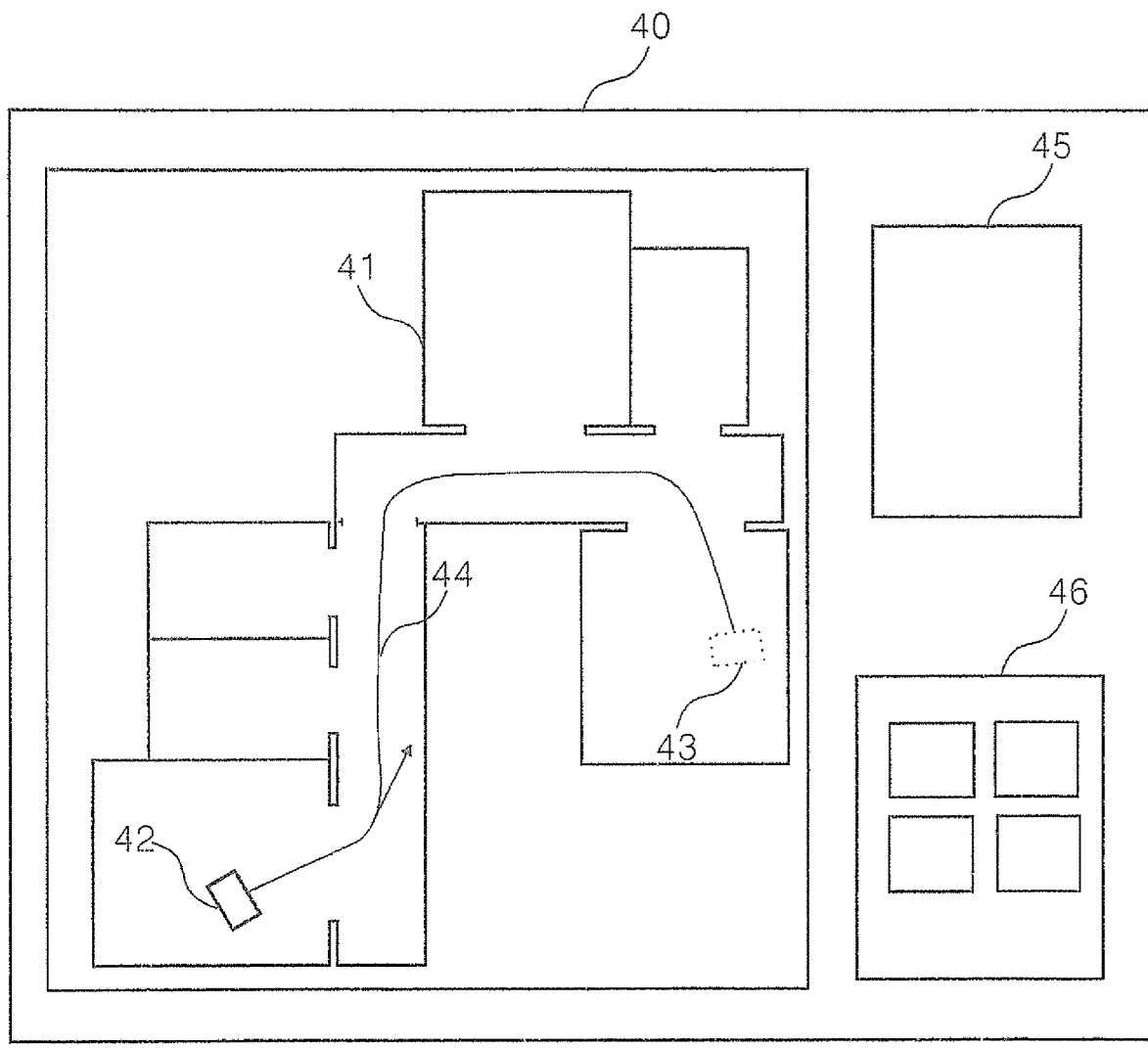
FIG. 4 is a schematic illustration of a man-machine interactive interface of a mobile X-ray examination apparatus according to an embodiment of the present invention.

FIG. 4 is a schematic illustration of a man-machine interactive interface of a mobile X-ray examination apparatus according to an embodiment of the present invention. As FIG. 4 shows, the man-machine interactive interface 40 is for example a touch display screen, on which are presented an environment map 41 of the environment in which the mobile X-ray examination apparatus 10 is used, the current position 42 of the mobile X-ray examination apparatus 10, the designated position 43 to be reached, and a movement trajectory 44. In addition, the man-machine interface 40 has an apparatus-related information region 45 and a button region 46. The apparatus-related information region 45 is mainly used for displaying certain relevant state information in the process of navigation, such as current electrical energy reserves of the apparatus, current movement speed of the apparatus, recent obstacle bearings etc. The button region is used to achieve selection and parameter change of certain functions, such as pause/continue/stop current navigation, maximum traveling speed setting, clear alert information etc. The man-machine interactive interface comprises the instruction receiving device 11, and can allow a user to enter a corresponding setting interface, to set the designated position to be reached.

By means of an instruction given to the mobile X-ray examination apparatus of the present invention by a doctor, the mobile X-ray examination apparatus can itself move from one room to another intelligently; users can be completely freed from arduous moving work, making their work less intensive and improving their working efficiency. Real-time navigation information can be presented as required and can be fed back to a server; this suits informatization of hospitals. The navigation function may be designed as a removable device. Through the use of a modular design, examination instruments in the same class may share a single navigation device.

The above embodiments are merely preferred embodiments of the present invention, which are not intended to limit it. Any amendments, equivalent substitutions or improvements etc. made within the spirit and principles of the present invention shall be included in the scope of protection thereof.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A mobile X-ray examination apparatus, comprising:
an apparatus body with an X-ray source and an X-ray detector mounted thereon, said apparatus body comprising a drive device and a transport device;
an instruction receiving device situated on the apparatus body, the instruction receiving device being configured to receive an instruction configured to be entered therein as an input, and configured to instruct the apparatus body to reach a designated position;
a navigation device removably mounted on the apparatus body, to which the instruction receiving device sends the instruction, the navigation device including a detection device comprising an optical detection and distance-measuring sensor, the optical detection and distance-measuring sensor being mounted so as to face a region in front of the apparatus body in a direction of travel thereof, the optical detection and distance-measuring sensor being configured to emit a series of coded laser pulses at intervals of a predetermined angle in a plane in space so as to detect, in real time, the environment of the mobile X-ray examination apparatus,
wherein said navigation device is configured to create an environment map of an environment of the mobile X-ray examination apparatus, and to determine a current position of the apparatus body according to a detected environment profile information;
said navigation device being further configured to calculate a movement trajectory of the apparatus body according to the environment map, the current position, and the designated position received from the instruction receiving device; and
a central control device situated on the apparatus body,
wherein said navigation device is configured to send an electronic designation of the calculated movement trajectory to said central control device,
wherein said central control device is configured to operate said drive device that in turn drives said transport device of the apparatus body to follow the calculated movement trajectory so as to reach the designated position, and
wherein the navigation device is connected, when mounted on the apparatus body, to the central control device via an interface that provides connections to power the navigation device and to enable communications between the navigation device and the central control device.

2. The mobile X-ray examination apparatus as claimed in claim 1, wherein:
the navigation device further comprises a navigation controller configured to calculate relative positions of an obstacle and the apparatus body according to an angle of a laser pulse emitted by the optical detection and distance-measuring sensor and a time difference between emission of the laser pulse and back-reflection thereof by the obstacle after encountering the obstacle, to find a route by which the obstacle can be avoided.

3. The mobile X-ray examination apparatus as claimed in claim 2, comprising:
a notification device configured to issue prompt information when the navigation device cannot find a route by which an obstacle can be avoided.

4. The mobile X-ray examination apparatus as claimed in claim 1, wherein:
the navigation device is configured to obtain profile information about surrounding obstacles according to (i) a laser pulse emitted by the optical detection and distance-measuring sensor and a laser pulse that is reflected back, and (ii) the profile information, and to perform matching with the environment map to locate the apparatus body in said environment.

5. The mobile X-ray examination apparatus as claimed in claim 1, further comprising:
   a movement device configured to produce real-time movement information of the movement of the apparatus body,
   wherein the navigation device is configured to determine the current position of the apparatus body, which is used to calculate the movement trajectory of the apparatus body, according to said real-time movement information of the movement device.

6. The mobile X-ray examination apparatus as claimed in claim 1, wherein:
   the navigation device is configured to create the environment map by offline importing.

7. The mobile X-ray examination apparatus as claimed in claim 1, wherein:
   said drive device is a DC motor or a hub motor.

8. The mobile X-ray examination apparatus as claimed in claim 1, wherein the navigation device is configured to create the environment map by detecting the environment of said mobile X-ray examination apparatus as said mobile X-ray examination apparatus is manually moved along said movement trajectory.

9. The mobile X-ray examination apparatus as claimed in claim 1, wherein the navigation device is configured to receive parameter settings to match corresponding parameters associated with the mobile X-ray examination apparatus.

10. The mobile X-ray examination apparatus as claimed in claim 9, wherein the parameter settings received by the navigation device include at least one of a model number and a motor parameter associated with the mobile X-ray examination apparatus.

11. The mobile X-ray examination apparatus as claimed in claim 10, wherein the navigation device is configured to be removably mounted to a plurality of different mobile X-ray examination apparatuses, the navigation device being configured to receive different parameter settings to operate with each respective one of the mobile X-ray examination apparatuses.

12. The mobile X-ray examination apparatus as claimed in claim 1, wherein the navigation device is configured to create the environment map by detecting the environment of said mobile X-ray examination apparatus as said mobile X-ray examination apparatus is manually moved so as to traverse, at least once, each of a plurality of reachable positions in the environment of the mobile X-ray examination apparatus.

13. The mobile X-ray examination apparatus as claimed in claim 1, wherein the navigation device is removably mounted on the apparatus body via a modular design.

* * * * *